US00PP29293P2

(12) United States Plant Patent
Selten

(10) Patent No.: US PP29,293 P2
(45) Date of Patent: May 15, 2018

(54) *NANDINA* PLANT NAMED 'SELTEN004'

(50) Latin Name: *Nandina domestica*
Varietal Denomination: Selten004

(71) Applicant: Johannes C. M. Selten, Horst (NL)

(72) Inventor: Johannes C. M. Selten, Horst (NL)

( * ) Notice: Subject to any disclaimer, the term of this patent is extended or adjusted under 35 U.S.C. 154(b) by 0 days. days.

(21) Appl. No.: 15/330,424

(22) Filed: Sep. 19, 2016

(51) Int. Cl.
*A01H 5/02* (2018.01)

(52) U.S. Cl.
USPC ..... Plt./235

(58) Field of Classification Search
USPC ..... Plt./235
See application file for complete search history.

(56) References Cited

PUBLICATIONS

UPOV hit on *Nandina* plant named 'Selten004', QZ PBR 2014/1341, filed May 15, 2014.*

* cited by examiner

*Primary Examiner* — Anne Marie Grunberg
(74) *Attorney, Agent, or Firm* — Penny J. Aguirre

(57) ABSTRACT

A new cultivar of *Nandina domestica* named 'Selten004', characterized by its bushy upright growing habit, its leaves that are light yellow-green in color, its palm-like leaves that are large in size, and its hardiness at least to U.S.D.A. Zone 7.

2 Drawing Sheets

Botanical classification: *Nandina domestica.*
Variety denomination: 'Selten004'.

CROSS REFERENCE TO A RELATED APPLICATION

This application is related to a European plant breeders' rights application filed on May, 15, 2014, application No. 2014/1341. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Nandina domestica* and will be referred to hereafter by its cultivar name, 'Selten004'. 'Selten004' is a new cultivar of *Nandina* shrub grown for use as a landscape plant.

The new cultivar was discovered as a branch mutation by the Inventor in 2001 in Horst, The Netherlands. The new cultivar arose as a naturally occurring branch mutation found on a plant derived from *Nandina domestica* 'Richmond'.

Asexual reproduction of the new cultivar was first accomplished by the inventor using softwood stem cuttings in 2011 in Horst, The Netherlands. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Selten004' as a unique cultivar of *Nandina.*

1. 'Selten004' exhibits a bushy upright growing habit.
2. 'Selten004' exhibits leaves that are light yellow-green in color.
3. 'Selten004' exhibits palm-like leaves that are large in size.
4. 'Selten004' exhibits hardiness at least to U.S.D.A. Zone 7.

'Richmond', the parent plant of 'Selten004' is similar to 'Selten004' in having flowers that are white in color, however 'Richmond' differs from 'Selten004' in having foliage that is darker green in color. 'Selten004' can be most closely compared to the cultivars 'Gulfstream' (U.S. Plant Pat. No. 5,656) and 'Compacta' (not patented). 'Gulfstream' differs from 'Selten004' in having a dwarf plant habit, in having a round plant shape and in having dense foliage. 'Compacta' differs from 'Selten004' in having foliage that is darker green in color, in having a larger plant height and width and in having a clumping plant habit as it matures.

BRIEF DESCRIPTION OF THE DRAWINGS

The accompanying colored photographs illustrate the overall appearance and distinct characteristics of three year-old plants of the new *Nandina* as grown outdoors in 3-gallon containers in Horst, The Netherlands.

The photograph in FIG. 1 illustrates the overall appearance of 'Selten004'.

Figure 1:
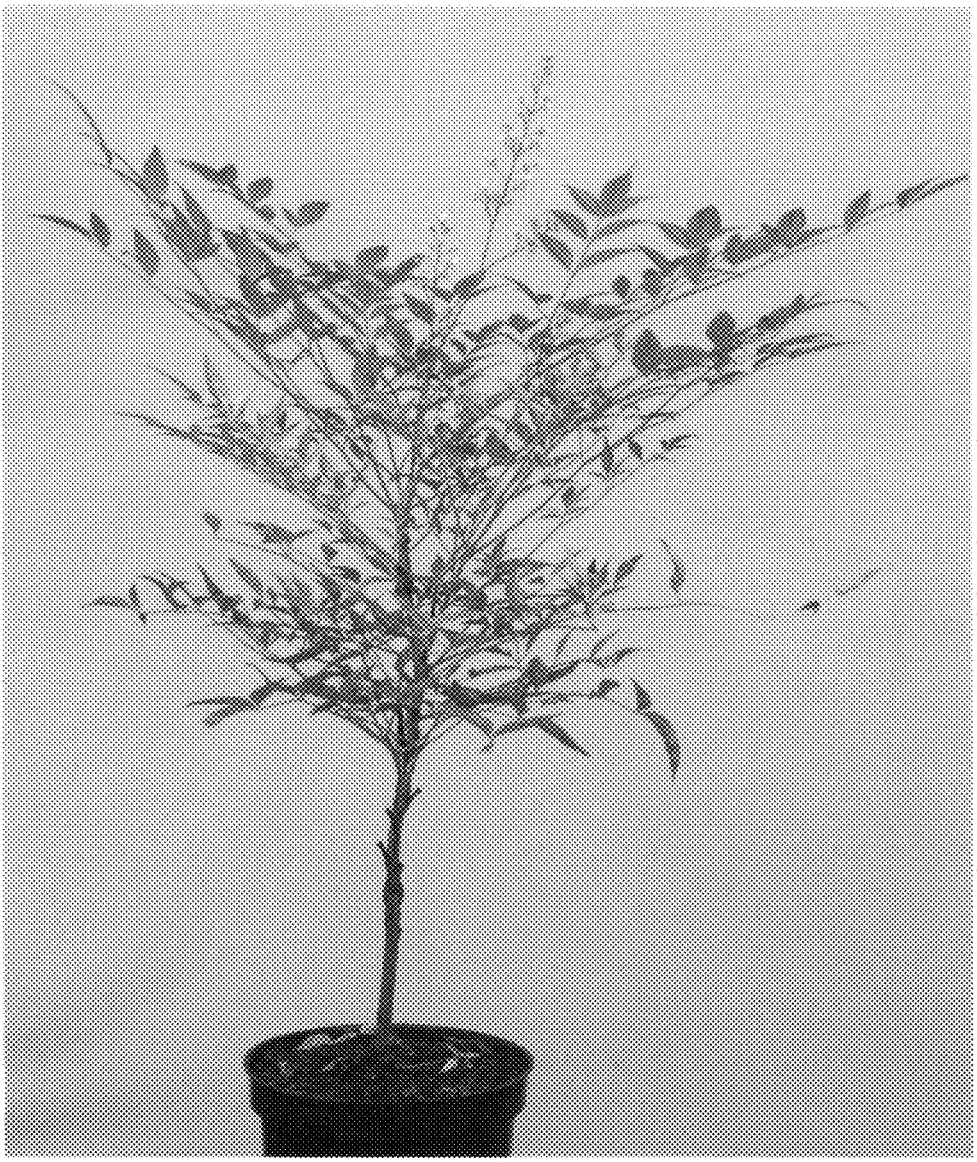
Figure 2:
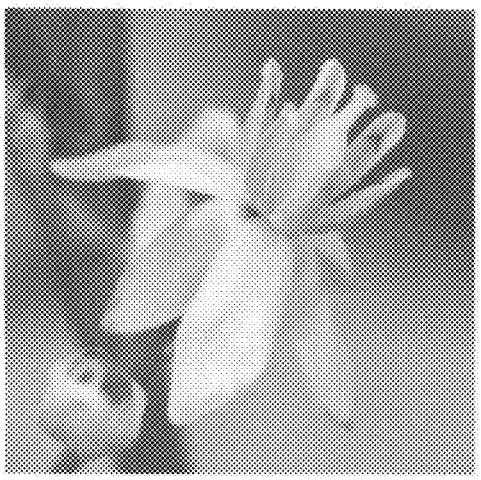

The photograph in FIG. 2 provides a close-up view of a flower of 'Selten004'.

Figure 3:
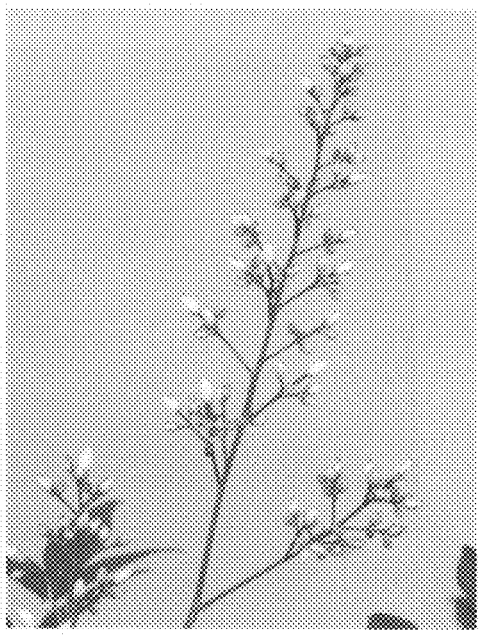

The photograph in FIG. 3 provides a view of the inflorescence of 'Selten004'.

Figure 4:
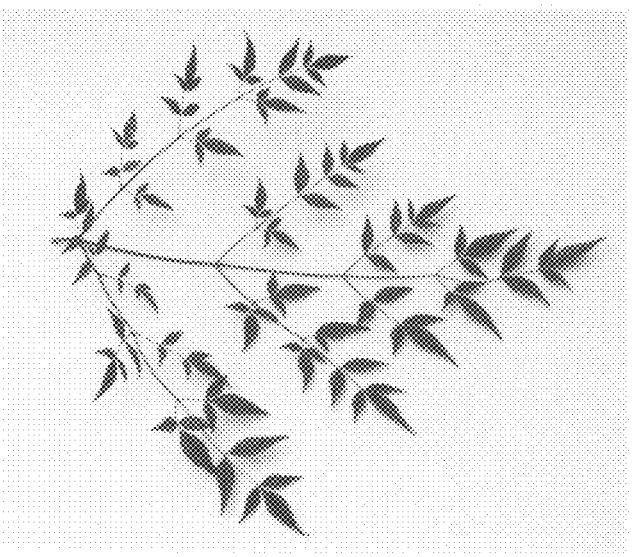

The photograph in FIG. 4 provides a close up view of a leaf of 'Selten004'.

The colors in the photographs are as close as possible with the digital photography techniques utilized and the color values cited in the detailed botanical description accurately describe the colors of the new *Nandina*.

DETAILED BOTANICAL DESCRIPTION

The following is a detailed description of a 2 year-old plant of the new cultivar as grown outdoors in a 22-cm container in June Horst, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen shrub.

*Plant habit*.—Upright and bushy.

*Height and spread*.—Average of 79.7 cm in height and 77.3 cm in width.

*Hardiness*.—At least in U.S.D.A. Zone 7.

*Diseases and pests*.—No susceptibility or resistance to diseases or pests has been observed.

*Root description*.—Fibrous and fleshy, a blend of 158B and 167C in color.

*Root habit*.—Outward spreading by underground rhizomes has not been observed.

*Propagation*.—Softwood stem cuttings.

*Growth rate*.—Moderate.

Stem description:

*Stem strength*.—Very strong.

*Stem color*.—Younger stems; 143C to 143D, mature stems and older bark; 199B.

*Stem size*.—Main stem; 47 cm in length and 7 mm in diameter, lateral branches; 7.7 cm in length and 4 mm in diameter.

*Stem surface*.—Moderately axially ribbed and dull.

*Stem aspect*.—Near vertical.

*Internode length*.—Average of 2.8 cm.

*Branching*.—1 main stem and an average of 2 lateral branches.

Foliage description:

*Leaf shape*.—Deltoid overall.

*Leaf division*.—Compound, tri-pinnate.

*Leaf arrangement*.—Alternate.

*Leaf number*.—On main stems an average of 8, on lateral stems an average of 2.

*Leaf size*.—Average of 50.7 cm in length and 60.9 cm in width.

*Leaf surface*.—Both sides glabrous, upper side slightly glossy, lower side matte.

*Leaf attachment*.—Petiolate.

*Leaflet base*.—Narrow acuminate.

*Leaflet apex*.—Narrowly acute.

*Leaflet shape*.—Ovate.

*Leaflet venation*.—Pinnate, upper surface color; 146A, lower surface color; 144B.

*Leaflet margins*.—Entire.

*Leaflet surface*.—Both sides glabrous, upper side slightly glossy, lower side matte.

*Leaflet size*.—Average of 5.9 cm in length and 1.9 cm in width.

*Leaflet number*.—Average of 5.9 cm in length and 1.9 cm in width.

*Leaf/leaflet color*.—Young leaves upper surface; 144A, young leaves lower surface; between 145A and 146D, mature leaves upper surface; between 144A and 146A, mature and fall leaves lower surface; 146D.

*Petioles*.—Main petiole; Average of 43.6 cm in length and 2 mm in diameter, 143B in color, surface is glabrous, secondary petiole; average of 10.7 cm in length and 1 mm in diameter, 143B in color, surface is glabrous.

Inflorescence description:

*Inflorescence type*.—Panicle.

*Inflorescence size*.—Average of 30.2 cm in height and 10.1 cm in width.

*Inflorescence quantity*.—Average of 5 per plant in a 22-cm container.

*Flower quantity*.—Average of 135 flowers per inflorescence, 100 per lateral stem.

*Blooming habit*.—Once a year, continuously.

*Blooming season*.—Late spring into early summer.

*Blooming response time and rate*.—Average of 9 months, all flowers in an inflorescence have opened within four weeks.

*Fragrance*.—None.

*Flower buds*.—Average of 8 mm in length and 4 mm in diameter, ovate in shape, aspect is upright to slightly outward and 155C in color.

*Flowers*.—Shape is rotate, single, average of 1.3 cm in diameter and depth, longevity on plant is an average of 3 days, self cleaning.

*Petals*.—An average of 5, rotate in arrangement, appearance is slightly concave, surface texture on in and outer surfaces are glabrous and have a very slightly velvety texture, un-fused, ovate in shape, entire margins, acute apex, 8 mm in length and 3.5 mm in width, color when inner and outer surfaces are opening; 155C, not fading, color when inner and outer surfaces are fully open; NN155D, not fading.

*Sepals*.—Average of 15, concave appearance, spirally placed below petals which are dropped when flower opens, broad ovate in shape, entire margins, broad acute apex, broad cuneate base, 3.5 mm in length and 2 mm in width, inner and outer surfaces are glabrous and have a very slightly velvety texture, immature inner and outer surfaces color; 155C, mature inner and outer surfaces color; NN155C.

*Calyx*.—Rotate in shape, no mature calyx are present due to sepals being dropped when flower opens.

*Peduncle*.—Average of 29.5 cm in length and 2 mm in diameter, surface is glabrous, held at an average angle of 30° to stem, secondary peduncles held in an average angle of 40° to main peduncle, very strong and 143C in color.

*Pedicel*.—Average of 2 mm in length, 0.75 mm in diameter, surface is glabrous, pedicels held in an average angle of 45° to peduncle, very strong and 143C in color.

Reproductive organs:

*Gynoecium*.—1 pistil, average of 1.2 mm in length, stigmas; club-shaped, fringed an average of <0.5 mm in length and 150C in color, style; 0.5 mm in length and 150C in color, ovary; round in shape, 0.5 mm in length, 150D in color.

*Androecium*.—Stamens; average of 6, anthers; linear in shape, 5 mm in length and 13B in color; filaments;

0.75 mm in length and 11C in color, pollen; very low in quantity and 12B in color.

*Fruit/seeds*.—No fruit or seed production was observed to date.

It is claimed:

1. A new and distinct cultivar of *Nandina* plant named 'Selten004' as herein illustrated and described.

* * * * *